(12) United States Patent
Benson

(10) Patent No.: US 11,426,119 B2
(45) Date of Patent: Aug. 30, 2022

(54) ASSESSMENT OF SPINAL COLUMN INTEGRITY

(71) Applicant: WARSAW ORTHOPEDIC, INC., Warsaw, IN (US)

(72) Inventor: Nicholas M. Benson, Collierville, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 194 days.

(21) Appl. No.: 16/845,788

(22) Filed: Apr. 10, 2020

(65) Prior Publication Data

US 2021/0315515 A1 Oct. 14, 2021

(51) Int. Cl.
| | |
|---|---|
| G06K 9/00 | (2022.01) |
| A61B 5/00 | (2006.01) |
| G06T 7/00 | (2017.01) |
| A61B 34/10 | (2016.01) |

(52) U.S. Cl.
CPC .......... *A61B 5/4566* (2013.01); *A61B 5/4509* (2013.01); *A61B 5/742* (2013.01); *A61B 34/10* (2016.02); *G06T 7/0016* (2013.01); *A61B 2034/105* (2016.02); *G06T 2207/10081* (2013.01); *G06T 2207/30012* (2013.01)

(58) Field of Classification Search
CPC .................................................. A61B 5/4566
See application file for complete search history.

(56) References Cited

U.S. PATENT DOCUMENTS

| | | | |
|---|---|---|---|
| 5,270,654 A | 12/1993 | Feinberg et al. | |
| 6,608,916 B1 | 8/2003 | Wei et al. | |
| 6,711,432 B1* | 3/2004 | Krause | A61B 90/36 |
| | | | 600/426 |
| 2007/0036416 A1 | 2/2007 | Tsai et al. | |
| 2007/0223799 A1 | 9/2007 | Weiss | |
| 2009/0202122 A1 | 8/2009 | Wang | |
| 2009/0240137 A1 | 9/2009 | Rosa | |
| 2010/0086185 A1 | 4/2010 | Weiss | |
| 2012/0143990 A1 | 6/2012 | Hay et al. | |

(Continued)

FOREIGN PATENT DOCUMENTS

| | | |
|---|---|---|
| CN | 108492874 | 9/2018 |
| CN | 109934824 | 6/2019 |

(Continued)

OTHER PUBLICATIONS

U.S. Appl. No. 16/842,380, filed Apr. 7, 2020, Junio.

(Continued)

*Primary Examiner* — Oneal R Mistry
(74) *Attorney, Agent, or Firm* — Sheridan Ross P.C.

(57) ABSTRACT

A method of assessing spinal column stability involves receiving image data corresponding to a spinal column of a patient; determining, based on the image data, a material strength of bony anatomy in at least a portion of the spinal column; completing a first stability assessment of the spinal column, based at least in part on the determined material strength; modifying the image data to simulate removal of bony anatomy or soft tissue from the spinal column to yield modified image data; and completing a second stability assessment of the spinal column, based at least in part on the determined material strength and the modified image data.

20 Claims, 7 Drawing Sheets

(56) References Cited

U.S. PATENT DOCUMENTS

| | | | |
|---|---|---|---|
| 2012/0172700 A1 | 7/2012 | Krishman et al. | |
| 2013/0191154 A1* | 7/2013 | William R. | G16H 10/60 705/3 |
| 2014/0064583 A1 | 3/2014 | Wang et al. | |
| 2014/0081659 A1 | 3/2014 | Nawana et al. | |
| 2015/0173701 A1 | 6/2015 | Major et al. | |
| 2015/0182288 A1* | 7/2015 | Greenwald | A61B 34/30 606/279 |
| 2015/0248593 A1 | 9/2015 | Nakashima et al. | |
| 2015/0254839 A1 | 9/2015 | Yoo | |
| 2015/0356729 A1 | 12/2015 | Hladuvka et al. | |
| 2016/0267655 A1 | 9/2016 | Akahori | |
| 2016/0364862 A1 | 12/2016 | Reicher et al. | |
| 2017/0252107 A1* | 9/2017 | Turner | G16H 50/50 |
| 2019/0021677 A1 | 1/2019 | Grbic et al. | |
| 2020/0038111 A1 | 2/2020 | Turner et al. | |
| 2020/0315708 A1* | 10/2020 | Mosnier | G16H 10/20 |

FOREIGN PATENT DOCUMENTS

| | | | |
|---|---|---|---|
| JP | 2010-029482 | 2/2010 | |
| JP | 6582171 | 9/2019 | |
| KR | 10-2014-0064583 | 5/2014 | |
| KR | 102062539 | 1/2020 | |
| WO | WO 2019/012520 | 6/2012 | |
| WO | WO-2018109556 A1 * | 6/2018 | A61B 17/7011 |
| WO | WO-2020079598 A1 * | 4/2020 | A61B 34/10 |

OTHER PUBLICATIONS

Al Kafri et al., "Segmentation of Lumbar Spine MRI Images for Stenosis Detection Using Patch-Based Pixel Classification Neural Network," 2018 IEEE Congress on Evolutionary Computation, Jul. 2018, 8 pages.

Al Kafri, "Boundary Delineation of MRI Images for Lumbar Spinal Stenosis Detection through Semantic Segmentation Using Deep Neural Networks," IEEE Access, vol. 7, Apr. 1, 2019, pp. 433487-443501.

Chen et al., "Automatic Localization and Identification of Vertebrae in Spine CT via a Joint Learning Model with Deep Neural Networks," International Conference on Medical Image Computing and Computer-Assisted Intervention, Nov. 2015, pp. 512-522. Abstract only.

Gawel et al., "Automatic Spine Tissue Segmentation from MRI Data Based on Cascade of Boosted Classifiers and Active Appearance Model," BioMed Research International, vol. 2018, No. 7952946, Apr. 2018, 13 pages.

Kim et al., "Automatic detection and segmentation of lumbar vertebra from X-ray images for compression fracture evaluation," arXiv ePrint, vol. 1904.07624v1, Apr. 16, 2019, 18 pages.

Koompairojn et al., "Computer-Aided Diagnosis of Lumbar Stenosis Conditions," Proceedings of SPIE—The International Society for Optical Engineering, vol. 7624, Mar. 2010, 12 pages.

Lu et al., Deep Spine: Automated Lumbar Vertebral Segmentation, Disc-Level Designation, and Spinal Stenosis Grading Using Deep Learning, Proceedings of Machine Learning Research, vol. 85, Jul. 2018, 16 pages.

Neubert et al., "Automated detection, 3D segmentation and analysis of high resolution spine MR images using statistical shape models," Physics in Medicine & Biology, vol. 57, No. 24, Dec. 2012, pp. 7357-8376.

Qadri et al., "Automatic Deep Feature Learning via Patch-Based Deep Belief Network for Vertebrae Segmentation in CT Images," Applied Sciences, vol. 9, No. 69, 2019, 17 pages.

Steiner et al., "Patient-Specific In Silico Models Can Quantify Primary Implant Stability in Elderly Human Bone," Journal of Orthopaedic Research, vol. 36, Mar. 2018, pp. 954-962.

Suzani et al., "Deep Learning for Automatic Localization, Identification, and Segmentation of Vertebral Bodies in Volumetric MR Images," SPIE Medical Imaging 2015: Image-Guided Procedures, Robotic Interventions, and Modeling, vol. 9415-15, Feb. 2015, 7 pp.

Wang et al., Automatic Segmentation of Spinal Canals in CT Images via Iterative Topology Refinement, IEEE Transactions on Medical Imaging, vol. 34, No. 8, Aug. 2015, pp. 1694-1704.

Ito et al. "Step-by-Step Sublaminar Approach With a Newly-Designed Spinal Endoscope for Unilateral-Approach Bilateral Decompression in Spinal Stenosis," Neurospine, 2019, vol. 16, No. 1, pp. 41-51.

Lee et al. "The anatomy of the thoracic spinal canal investigated with magnetic resonance imaging (MRI)," Acta Anaesthesiologica Belgica, Sep. 2007, vol. 58, No. 3, pp. 163-167.

Maher et al. "Lateral exit-zone stenosis and lumbar radiculopathy," Journal of Neurosurgery: Spine, Jan. 1999, vol. 90, pp. 52-58.

Ulbrich et al. "Normative MR Cervical Spinal Canal Dimensions," Radiology, Apr. 2014, vol. 271, No. 1, pp. 172-182.

Official Action for U.S. Appl. No. 16/842,380, dated Nov. 26, 2021 32 pages.

* cited by examiner

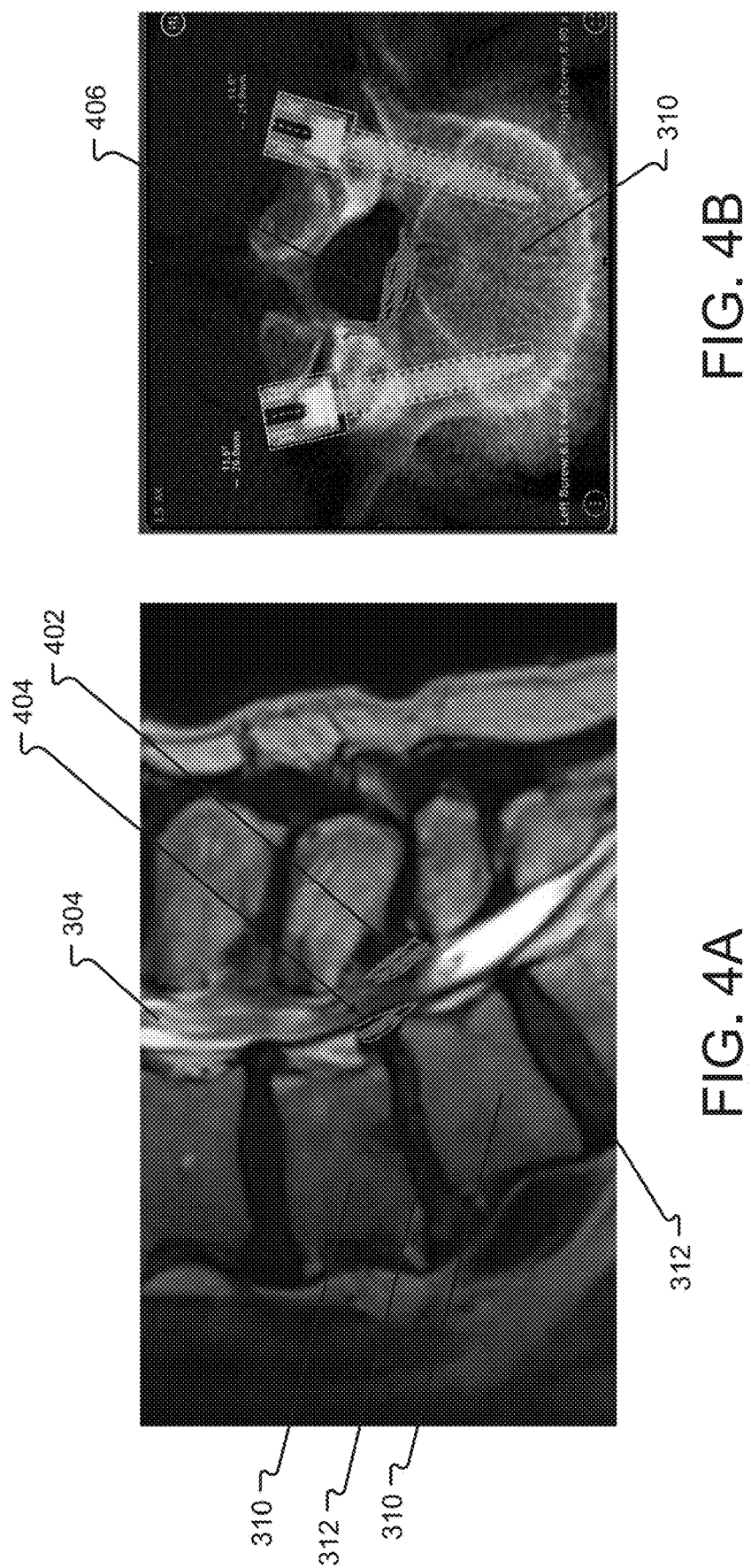

ASSESSMENT OF SPINAL COLUMN INTEGRITY

FIELD

The present technology is related generally to decompression treatment and, more particularly, to evaluation of the effect of decompression treatment on spinal column integrity.

BACKGROUND

Lumbar spinal stenosis, or compression of neural elements due to a narrowing of the spinal canal, is one of the largest contributors to spinal procedures in patients over 65. Spinal decompression procedures for relieving a spinal compression are delicate, time consuming, and high-risk tasks. Diagnosis of spinal stenosis is typically accomplished using a combination of patient imaging, patient verbal inputs, patient reported function and physical examination of the patient. Once diagnosed, spinal stenosis may be treated with non-invasive means such as massages, chiropractic treatments, and/or acupuncture, and/or with invasive procedures including laminectomy, laminotomy, discectomy, and so forth.

Access to and removal of bony anatomy and/or soft tissue from the spinal column can affect the integrity of the spinal column, including the stability and/or mobility of the spinal column. Iatrogenic instability is instability of the spinal column resulting from surgical or medical intervention and can negatively affect a patient's quality of life.

Conventional methods for assessing spinal column integrity (including the risk that a given procedure will cause iatrogenic instability) rely on a surgeon's prior experience, knowledge, and judgment. Such conventional methods are time consuming, subjective, complex, and may not be recorded for future reference or use. Whether spinal fusion or other methods of improving spinal column integrity are needed as a result of decompression or other spinal surgery is a subjective determination.

SUMMARY

Embodiments of the present disclosure advantageously provide objective approaches to assessing the effect of a decompression procedure or other spinal surgery on spinal stability, including in particular for assessing the risk that a given decompression or other spinal surgery will result in iatrogenic instability. Embodiments of the present disclosure thus beneficially augment the treating physician's prior experience, knowledge, and judgment with objective data. Embodiments of the present disclosure may also beneficially enable a treating physician to assess the effect of one or more possible decompressions or other spinal surgery procedures on spinal column integrity, select a procedure with a least negative impact on spinal column integrity, and/or prepare for a spinal fusion or other stability-enhancing procedure in advance of a surgical procedure that is expected to negatively affect spinal column integrity.

A method of assessing spinal column stability according to one embodiment of the present disclosure comprises: receiving image data corresponding to a spinal column of a patient; determining, based on the image data, a material strength of bony anatomy in at least a portion of the spinal column; completing a first stability assessment of the spinal column, based at least in part on the determined material strength; modifying the image data to simulate removal of bony anatomy or soft tissue from the spinal column to yield modified image data; and completing a second stability assessment of the spinal column, based at least in part on the determined material strength and the modified image data.

The method may further comprise comparing the second stability assessment to the first stability assessment and causing information corresponding to the comparison to be displayed via a user interface. The method may further comprise comparing the second stability assessment to a predetermined threshold and causing information corresponding to the comparison to be displayed via a user interface. The information corresponding to the comparison may be an indication that a risk of instability is high, medium, or low. The image data may correspond to a 3D image of the spinal column, the 3D image comprising a plurality of slices, and the determining may comprise determining a material strength of bony anatomy in each of the plurality of slices.

The simulated removal of bony anatomy or soft tissue from the spinal column may correspond to a received user selection of one of a laminectomy, a laminotomy, or a foraminotomy. The simulated removal of bony anatomy or soft tissue from the spinal column may correspond both to removal of first bony anatomy or soft tissue from the spinal column to correct stenosis, and to removal of second bony anatomy or soft tissue from the spinal column to enable access to the first bony anatomy or soft tissue.

The image data may correspond to a plurality of 2D images of the spinal column. The image data may correspond to a CT scan, and determining the material strength of bony anatomy in at least the portion of the spinal column may be based on a measurement in Hounsfield units of the bony anatomy.

A method of assessing spinal column stability according to another embodiment of the present disclosure comprises: receiving image data corresponding to a spinal column of a patient; receiving mobility data corresponding to an initial mobility assessment of the spinal column; modifying, based on a user input, the image data to simulate removal of bony anatomy or soft tissue from the spinal column to yield modified image data; and generating an updated mobility assessment of the spinal column, based on the modified image data.

The method may further comprise automatically analyzing the image data to identify stenosis in the spinal column. The automatic analysis may be based on a comparison of image data corresponding to a first portion of the spinal column to image data corresponding to a second portion of the spinal column, the second portion different than the first portion. The automatic analysis may utilize a predefined algorithm. The simulated removal of bony anatomy or soft tissue from the spinal column may be based on the identified stenosis. The user input may correspond to a user selection of one of a laminectomy, a laminotomy, or a foraminotomy. The simulated removal of bony anatomy or soft tissue from the spinal column may correspond both to removal of first bony anatomy or soft tissue from the spinal column to correct stenosis, and to removal of second bony anatomy or soft tissue from the spinal column to enable access to the first bony anatomy or soft tissue.

A system for assessing spinal column stability according to yet another embodiment of the present disclosure comprises: a communication interface; a processor; and a memory. The memory stores instructions for execution by the processor that, when executed, cause the processor to: receive preoperative image data corresponding to a spinal column of a patient in a first state; identify spinal stenosis based on the preoperative image data; determine a portion of bony anatomy or soft tissue to remove to correct the spinal stenosis; simulate removal of the portion of bony anatomy or soft tissue to yield modified preoperative image data; and generate a first stability assessment of the spinal column based on the modified preoperative image data.

The memory may store additional instructions that, when executed, further cause the processor to: receive postoperative image data corresponding to the spinal column of the patient, the postoperative image data reflecting removal of some bony anatomy or soft tissue relative to the preoperative image data; generate a second stability assessment of the spinal column based on the postoperative image data; generate a decompression surgical plan to correct the spinal stenosis; cause the decompression surgical plan to be displayed on a user interface; and/or determine a spinal column level of the spinal stenosis.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_0$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 4A is another lateral image of a spine region according to at least one embodiment of the present disclosure;

FIG. 4B is a superior image of a vertebra within the spine region of FIG. 4A, according to at least one embodiment of the present disclosure;

DETAILED DESCRIPTION

Figure 1:
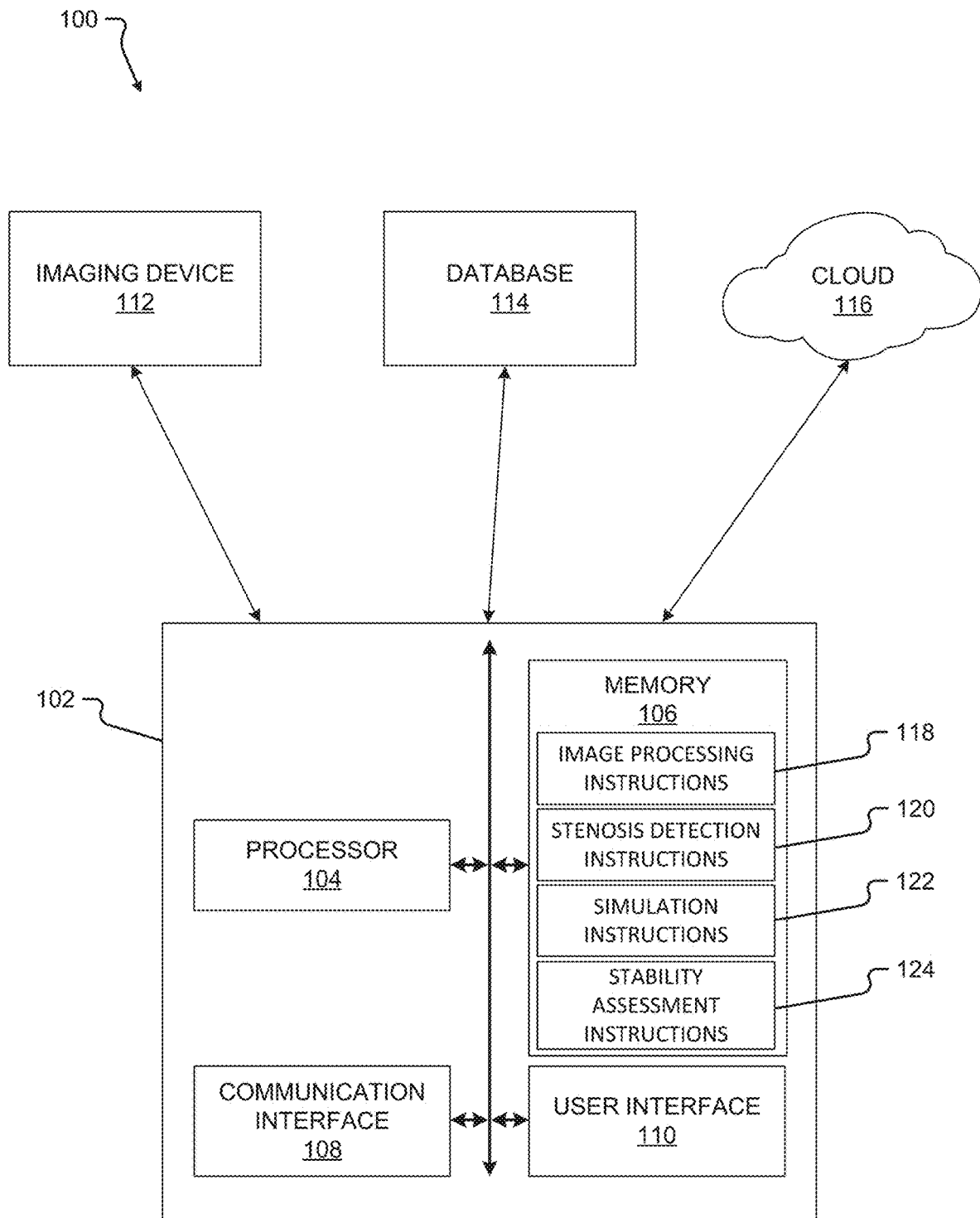
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Turning first to FIG. 1, a block diagram of a system 100 according to at least one embodiment of the present disclosure is shown. The system 100 may be used to process image data, detect spinal stenosis, carry out one or more virtual simulations, assess spinal column integrity, generate a decompression plan, generate a fusion plan, and/or carry out other aspects of one or more of the methods disclosed herein. The system 100 comprises a computing device 102, an imaging device 112, a database 114, and/or a cloud or other network 116. The computing device 102 comprises a processor 104, a memory 106, a communication interface 108, and a user interface 110. Systems such as the system 100 according to other embodiments of the present disclosure may comprise more or fewer components than the system 100.

The processor 104 of the computing device 102 may be any processor described herein or any similar processor. The processor may be configured to execute instructions stored in the memory 106, which instructions may cause the processor to carry out one or more computing steps utilized or based on data received from the imaging device 112, the database 114, and/or the cloud 116.

The memory 106 may be or comprise RAM, DRAM, SDRAM, other solid-state memory, any memory described herein, or any other non-transitory memory for storing computer-readable data and/or instructions. The memory 106 may store information or data useful for completing any step of any of the methods 200, 600, 600 and/or 800 described herein. The memory may store, for example, image processing instructions 118, stenosis detection instructions 120, simulation instructions 122, and/or stability assessment instructions 124. Such instructions may, in some embodiments, be organized into one or more applications, modules, packages, layers, or engines. The instructions may cause the processor 104 to manipulate data stored in the memory 106 and/or received from the imaging device 112, the database 114, and/or the cloud 116.

The computing device 102 may also comprise a communication interface 108. The communication interface 108 may be used for receiving image data or other information from an external source (such as the imaging device 112, the database 114, and/or the cloud 116), and/or for transmitting simulation results, decompression plans, fusion plans, images, or other information to an external source (e.g., the database 114, the cloud 116, another computing device 102). The communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, touchscreen, and/or any other device for receiving information from a user and/or for providing information to a user. The user interface 110 may be used, for example, to receive a user selection or other user input regarding a decompression procedure to simulate and/or plan; to receive a user selection or other user input regarding a type of approach to use to executed the decompression procedure; to receive user input regarding a portion of bony anatomy and/or soft tissue to remove to achieve decompression; to display a proposed decompression plan to a surgeon or other user; to display simulation results to a surgeon or other user; to display information corresponding to a stability assessment, a mobility assessment, or another spinal integrity assessment to a surgeon or other user; to display information about a risk of iatrogenic instability to a surgeon or other user; to display a decompression plan to a surgeon or other user; and/or to display a fusion plan to a surgeon or other user. In some embodiments, the user interface 110 may be useful to allow a surgeon or other user to modify a decompression plan, a fusion plan, or other displayed information.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 is operable to image an anatomy of a patient (e.g., a spine region) to yield image data (e.g., image data depicting a spinal column of a patient. The image data may correspond to the entire spinal column of the patient or to a portion of the spinal column of the patient. The imaging device 802 may be, but is not limited to, a magnetic resonance imaging (MRI) scanner, a CT scanner or other X-ray machine, an ultrasound scanner, an optical computed tomography scanner, or any other imaging device suitable for obtaining images of a spinal column of a patient.

The database 114 may store one or more images taken by one or more imaging devices 112 and may be configured to provide one or more such images (electronically, in the form of image data) to computing device such as the computing device 102. The database 114 may be configured to provide image data to a computing device 102 directly (e.g., when the computing device 102 and the database 114 are co-located, and/or are connected to the same local area network) and/or via the cloud 116 (e.g., when the computing device 102 and the database 114 are not co-located or otherwise connected to the same local area network). In some embodiments, the database 114 may be or comprise part of a hospital image storage system, such as a picture archiving and communication system (PACS), a health information system (HIS), and/or another system for collecting, storing, managing, and/or transmitting electronic medical records including image data.

The cloud 116 may be or represent the Internet or any other wide area network. The computing device 108 may be connected to the cloud 116 through the communication interface 108, via a wired or wireless connection. In some embodiments, the computing device 102 may communicate with the imaging device 112, the database 114, one or more other computing device 102, and/or one or more other components of a computing device 102 (e.g., a display or other user interface 110) via the cloud 116.

Turning now to FIGS. 2 through 5B, a method 200 according to embodiments of the present disclosure may be executed in whole or in part on a computing device 102.

The method 200 comprises receiving and processing preoperative image data (step 202). The preoperative image data may comprise or correspond to, for example, a three-dimensional image of a spinal column of a patient, and may comprise data corresponding to a plurality of individual cuts, slices, or sections of the spinal column of the patient that together make up the three-dimensional image of the spinal column. Additionally or alternatively, the preoperative image data may comprise or correspond to one or more two-dimensional images of the spinal column of the patient. For example, the preoperative image data may correspond to images such as the image 300 of FIG. 3A, and/or the image 302 of FIG. 3B. Where the image data comprises or corresponds to a plurality of two-dimensional images of the spinal column of the patient, the plurality of two-dimensional images may be sufficient to construct or reconstruct a three-dimensional image or model of the spinal column. The preoperative image data may correspond to a preoperative image taken of the spinal column of the patient using an imaging device 112, such as an MRI scanner, a CT scanner, or another imaging device. The preoperative image data may contain data for an entire spinal column of the patient or for a portion of the spinal column of the patient. The preoperative image data may be received from an imaging device 112, a database 114, the cloud 114, or any other source, and may be received via the communication interface 108.

Processing of the preoperative image data may include applying one or more filters to the image data to prepare the image data for further processing. Processing of the preoperative image data may also include segmenting the preoperative image data to identify, for example, one or more vertebrae 310, one or more discs 312, a spinal cord 304, and/or one or more nerve exits 306 represented by the image data. The segmenting may utilize feature identification, machine learning, or any other segmentation method. Additionally or alternatively, the processing may include measuring, inferring, calculating, or otherwise identifying one or more properties of the bony anatomy or soft tissue represented in the image data. For example, the processing may include determining a measurement in Hounsfield units of one or more vertebrae 310 or portions thereof and converting the measurement into a bone mineral density value or other value representative of the strength or stiffness of the bony anatomy in question. Any other measurement or algorithm may be utilized to measure, infer, calculate, or otherwise determine a strength or stiffness of one or more anatomical elements represented in the image data. In some embodiments, the processing yields a material strength or stiffness determination for a plurality of vertebra 310 represented in the image data, or for every vertebra 310 represented in the image data. Also in some embodiments, the in silico modeling and processing yields a material strength or stiffness determination for a plurality of discs 312 represented in the image data, or for every disc represented in the image data.

The method 200 also comprises identifying spinal stenosis based on the preoperative image data (step 204). The stenosis may be identified in the central canal and/or in a lateral recess of the spinal column represented by the image data. In some embodiments, the stenosis may be identified by comparing one or more attributes of the spinal cord 304 at one location of the spinal column represented in the image data with the corresponding one or more attributes of the spinal cord 304 at another location of the spinal column represented in the image data. For example, the stenosis may be identified by comparing a diameter of the spinal cord at a first level of the spinal column with a diameter of the spinal cord at one or more other levels of the spinal column, which one or more other levels may be adjacent the first level. A sudden or rapid change in the diameter of the spinal column between or among adjacent or proximate levels may indicate stenosis.

In other embodiments, the stenosis may be identified by applying a predetermined algorithm to the image data. The algorithm may be or have been generated, for example, by a machine learning engine based on training data.

In still other embodiments, a surgeon or other user may identify the stenosis by providing one or more inputs via a user interface 110. In such embodiments, the identification of the stenosis may be based on the image data and/or additional information obtained by otherwise known to the surgeon or other user, such as information provided by the patient or uncovered during a neurologic exam.

The method 200 further comprises determining one or more symptomatic levels of the spinal stenosis (step 206). In some embodiments, the identified stenosis may be located at only one level of the spinal column represented in the image data. In other embodiments, the identified stenosis may be located at a plurality of levels of the spinal column. Based on the processing of the image data in step 202, and/or the identification of the stenosis in step 204, the level(s) at which the stenosis exists may be determined and, in some embodiments, recorded (e.g., in a memory 106) and/or reported (e.g., via a user interface 110). The level(s) at which the stenosis exists is/are the target level(s) for purposes of steps 208 and 210.

The method 200 also comprises identifying bony anatomy and/or soft tissue to be removed at the target level(s) (step 208). Correction of spinal stenosis often involves decompression, or removal of bony anatomy and/or soft tissue that is compressing the spinal cord. In some embodiments, an algorithm is used to identify bony anatomy and/or soft tissue at the target level(s) that needs to be removed to create enough space for the spinal cord 304 to return to a normal diameter (or otherwise be freed from compression). For example, in FIGS. 4A-4B, the markings 402, 404, and 406 identify bony anatomy and/or soft tissue that needs to be removed to free the spinal cord 304 of compression. The bony anatomy may be, for example, a portion of one or more vertebrae 310, and the soft tissue may be, for example, all or part of a disc 312.

In some embodiments, the identifying of bony anatomy and/or soft tissue to be removed at the target level(s) may comprise receiving user input (e.g., from a surgeon or other user) via a user interface 110 that identifies the bony anatomy and/or soft tissue to be removed. For example, the user input may comprise a user selection of one of a laminotomy, laminectomy, foraminotomy, discectomy, or other procedure. Based on the user selection, a recommended portion of bony anatomy and/or soft tissue may be automatically identified for removal, or the surgeon or other user may identify the portion of bony anatomy and/or soft tissue to be removed. For example, if the user input is a laminectomy, a lamina of a vertebra 310 proximate the identified stenosis may be automatically identified for removal, or the user may select a lamina of a vertebra 310 for removal.

Often, the bony anatomy or soft tissue that needs to be removed in a decompression procedure is not readily accessible to a surgeon. As a result, the surgeon must remove additional bony anatomy and/or soft tissue from the spinal column simply to access the bony anatomy and/or soft tissue causing the stenosis. In some embodiments, then, identification of the bony anatomy and/or soft tissue to be removed includes not only identifying the bony anatomy and/or soft tissue that needs to be removed to correct the stenosis, but also identifying the optimal trajectory and/or bony anatomy and/or soft tissue that needs to be removed to access the stenosis-causing bony anatomy and/or soft tissue. The bony anatomy and/or soft tissue that must be removed to access the stenosis-causing bony anatomy and/or soft tissue may be identified automatically (e.g., by applying an algorithm selected based on the procedure to be completed and/or predefined by a machine learning engine or otherwise) or via additional user input via a user interface 110.

The identifying step 208 may further comprise marking the identified bony anatomy and/or soft tissue in the image data.

Figure 5B:
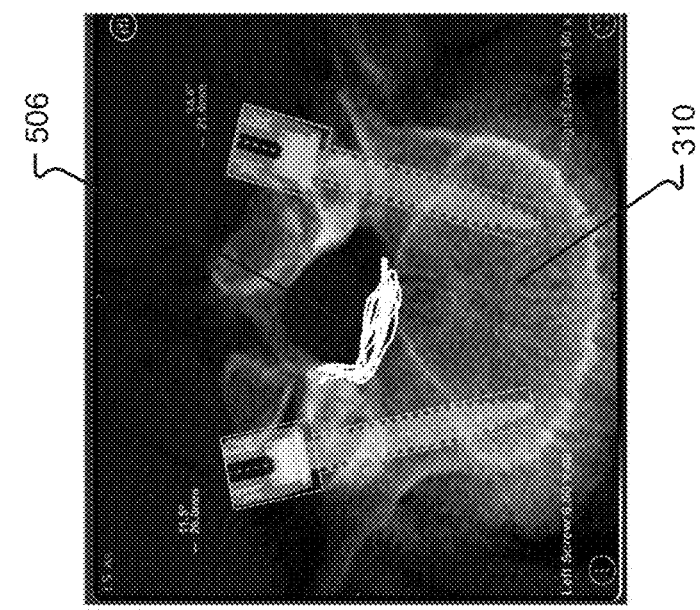
FIG. 5B is a superior image of a vertebra within the spine region of FIG. 4A, according to at least one embodiment of the present disclosure.
Figure 5A:
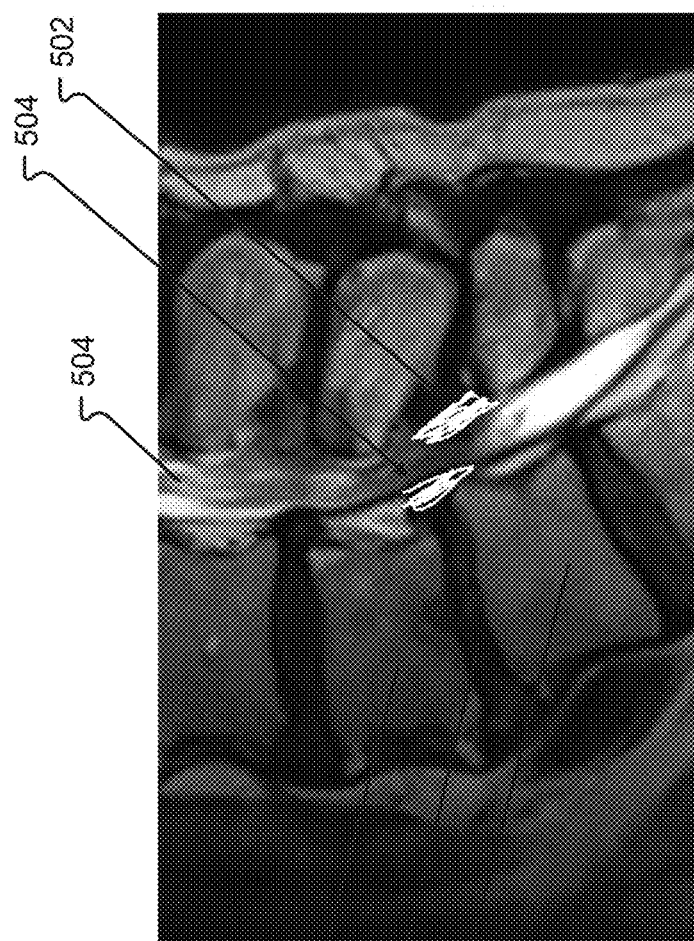
FIG. 5A is a lateral image of a spine region according to at least one embodiment of the present disclosure.

The method 200 further comprises virtually removing the bony anatomy and/or soft tissue at the target level(s) in a simulated decompression procedure, to yield modified preoperative image data (step 210). The virtual removal of the bony anatomy and/or soft tissue may comprise modifying the image data to substitute a virtual material having little or no strength or stiffness for the identified bony anatomy and/or soft tissue. Alternatively, the virtual removal of the bony anatomy and/or soft tissue may comprise simply deleting the portion of the image data representing the bony anatomy and/or the soft tissue to be removed. As another alternative, the virtual removal of the bony anatomy and/or soft tissue may comprise assigning a Hounsfield units measurement of zero to the portion of the image data representing the bony anatomy and/or the soft tissue to be removed. FIGS. 5A and 5B show removed portions 502, 504, and 506 of bony anatomy and/or soft tissue from an imaged spinal column.

The method 200 also comprises assessing a stability of the spinal column based on the modified preoperative image data (step 212). Assessing the stability of the spinal column may comprise, for example, running a virtual 6-degrees of motion analysis based on the modified preoperative image data to assess the predicted stability of the spine following the planned procedure. The analysis may evaluate the stresses that will be present in one or more vertebrae or section of vertebra of the spinal column represented in the modified preoperative image data while the spinal column is in a neutral position and/or while the spinal column is in one or more positions of flexion. In some embodiments, a virtual 6-degree of motion analysis may be conducted using the original preoperative image data, the results of which may be used as a reference for the virtual 6-degree of motion analysis conducted using the modified preoperative image data to assess how the planned procedure might affect the stability of the spine relative to its preoperative level of stability. In some embodiments, assessing the stability of the spinal column may be the same as or similar to conducting a finite element analysis on the spinal column (as it is represented in the modified preoperative image data).

The result of the assessment (whether conducting using a virtual 6-degrees of motion analysis or otherwise) may be a calculated level of predicted stability or instability of the spinal column (measured, for example, in millimeters of translation or angulation, in $N/m^2$, or otherwise); an indication of the predicted maximum stress that one or more vertebrae of the spinal column will experience; an indication that a predicted level of stress for one or more vertebrae of the spinal column exceeds or approaches a predetermined threshold; or any other indication relating to the predicted stability or instability of the spinal column represented in the modified preoperative image data if the planned procedure is carried out. In some embodiments, the result of the virtual 6-degrees of motion analysis may be an indication that a calculated risk of iatrogenic instability is high, medium, or low, which indication may be based on comparing a calculated or otherwise predicted iatrogenic instability to one or more predetermined thresholds.

The spinal column stability assessment of step 212 may also evaluate whether and/or how removal of bony anatomy and/or soft tissue from the spinal column during the planned procedure affects movement of the spine. For example, removal of bony anatomy and/or soft tissue from the spinal column may result in at least a portion of the spinal column being less constrained and able to move more freely. This, in turn, may affect the stresses imposed on one or more elements of the spinal column.

The method 200 further comprises determining a decompression plan and possibly an implant placement plan (step 214). The decompression plan may be a plan for carrying out the simulated procedure used to modify the preoperative data prior to conducting spinal column stability assessment in step 212. The decompression plan may include information about which bony anatomy and/or soft tissue to remove to correct an identified stenosis. The decompression plan may also include information about which bony anatomy and/or soft tissue to remove to gain access to the bony anatomy and/or soft tissue is causing the stenotic condition. The decompression plan may include an identification of which instruments or types of instruments to use for one or more steps of the planned decompression, the trajectory for the decompression, and/or the order of steps to carry out the planned decompression. The decompression plan may be generated automatically and then presented to a surgeon or other user for review, modification, and/or approval. Alternatively, the decompression plan may be generated through a combination of automatically generated recommendations and user input regarding, for example, a desired decompression procedure, a desired approach for carrying out the decompression procedure, and/or which portion or portions of bony anatomy and/or soft tissue to remove to correct the identified stenosis. As yet another alternative, the decompression plan may be generated based solely on user input.

The decompression plan may be a plan intended for execution manually, e.g., by a surgeon utilizing hand-operated tools. The decompression plan may alternatively be a plan intended for execution by a surgical robot, or with the assistance of a surgical robot.

In some embodiments, the step 214 may also comprise determining a fusion plan, based on the results of the assessment in step 212. For example, if the assessment determines that the planned decompression procedure will have little or no effect on the stability of the spinal column or the stresses that will be imposed on the vertebrae of the spinal column, and/or if the assessment determines that the risk of iatrogenic instability is low, then no fusion plan may be prepared. Alternatively, if the assessment determines that the planned decompression procedure will have a material effect on the stability of the spinal column or the stresses that will be imposed on the vertebrae of the spinal column, and/or if the assessment determines that the risk of iatrogenic instability is high, then a fusion plan may be prepared.

The fusion plan may be a plan for improving the predicted postoperative stability of the spinal column, whether through the use of a bone graft and/or a spinal implant (whether metal plates to secure two or more vertebrae together, or a rod secured to pedicle screws that are inserted in the vertebrae to be fused, or an artificial disc, or an intervertebral disc, or otherwise). As with the decompression plan, the fusion plan may be generated automatically and then presented to a surgeon or other user for review, modification, and/or approval. Alternatively, the fusion plan may be generated through a combination of automatically generated recommendations and user input. As yet another alternative, the fusion plan may be generated based solely on user input.

The method 200 also comprises causing a decompression plan to be displayed on a monitor or other user interface in an operating room (step 216). The decompression plan may be displayed on a monitor, overlaid on a lens using augmented reality, or other user interface in the operating room to facilitate execution of the decompression plan by a surgeon. The displayed decompression plan may be augmented with surgical navigation and/or other systems to assist the surgeon in removing the correct bony anatomy and/or soft tissue from the spinal column of the patient to correct the stenosis, and/or to gain access to the bony anatomy and/or soft tissue that is causing the stenosis. In some embodiments, the displayed decompression plan will be carried out manually, while in other embodiments, the displayed decompression plan will be carried out automatically (e.g., by a surgical robot). In still other embodiments, the displayed decompression plan may be carried out with robotic assistance.

The method 200 further comprises receiving and processing postoperative image data (step 218). The received postoperative image data may be obtained from an imaging device 112 in the operating room or elsewhere that is used to image the spinal column of the patient following the decompression procedure, and/or from a database 114 in which such an image has been stored, and/or via the cloud 116. The received postoperative image data may be processed in any of the same or similar ways described above with respect to processing of the image data in step 202. The receiving and processing of the postoperative image data may occur while the patient is still in the operating room and may occur as soon as the bony anatomy and/or soft tissue causing the identified stenosis has been removed.

The method 200 also comprises assessing a stability of the spinal column based on the postoperative image data (step 220). The assessing may be completed in any of the same or similar ways described above with respect to assessing a stability of the spinal column based on the modified postoperative image data in step 212. Additionally, the results of the assessment may be the same or similar types of results as described above in connection with step 212. The assessing may occur while the patient is still undergoing surgery.

The method 200 further comprises causing a surgical plan to be displayed on a monitor or other user interface in an operating room (step 222). Where the results of the assessment in step 220 indicate that the risk of iatrogenic instability is high, or otherwise indicate that the decompression procedure has compromised spinal integrity in a way that necessitates surgical implant placement or other corrective measures, the method 200 may display to a surgeon in the operating room an operative or surgical plan to facilitate execution of the plan by the surgeon. The displayed operative plan may be a surgical plan that was prepared in step 214, or an operative plan that is prepared based on the results of the assessment in step 220. In the former instance, the surgical plan may be modified by the surgeon or another user based on the results of the assessment in step 220. In the latter instance, the operative plan may be generated automatically, prepared with a combination of automated recommendations and user input, and/or prepared solely based on user input.

The method 200 beneficially allows a surgeon or other physician to respond in real time or near real time to a determined risk of iatrogenic instability resulting from a decompression procedure. The method 200 thus beneficially avoids situations in which a patient undergoes a first decompression operation, and then must return to the operating room and/or hospital to undergo a second fusion operation. The method 200 also beneficially provides an objective measure of a risk of iatrogenic instability, thus helping to relieve treating physicians of the burden of making a subjective determination as to whether fusion is needed (whether at the time of or immediately after a decompression procedure, or based on a subsequent diagnosis of iatrogenic instability).

Although described with respect to a correcting compression of a spinal cord 304, the method 200 may also be used in connection with correcting compression of a traversing or exiting nerve 306.

Figure 6:
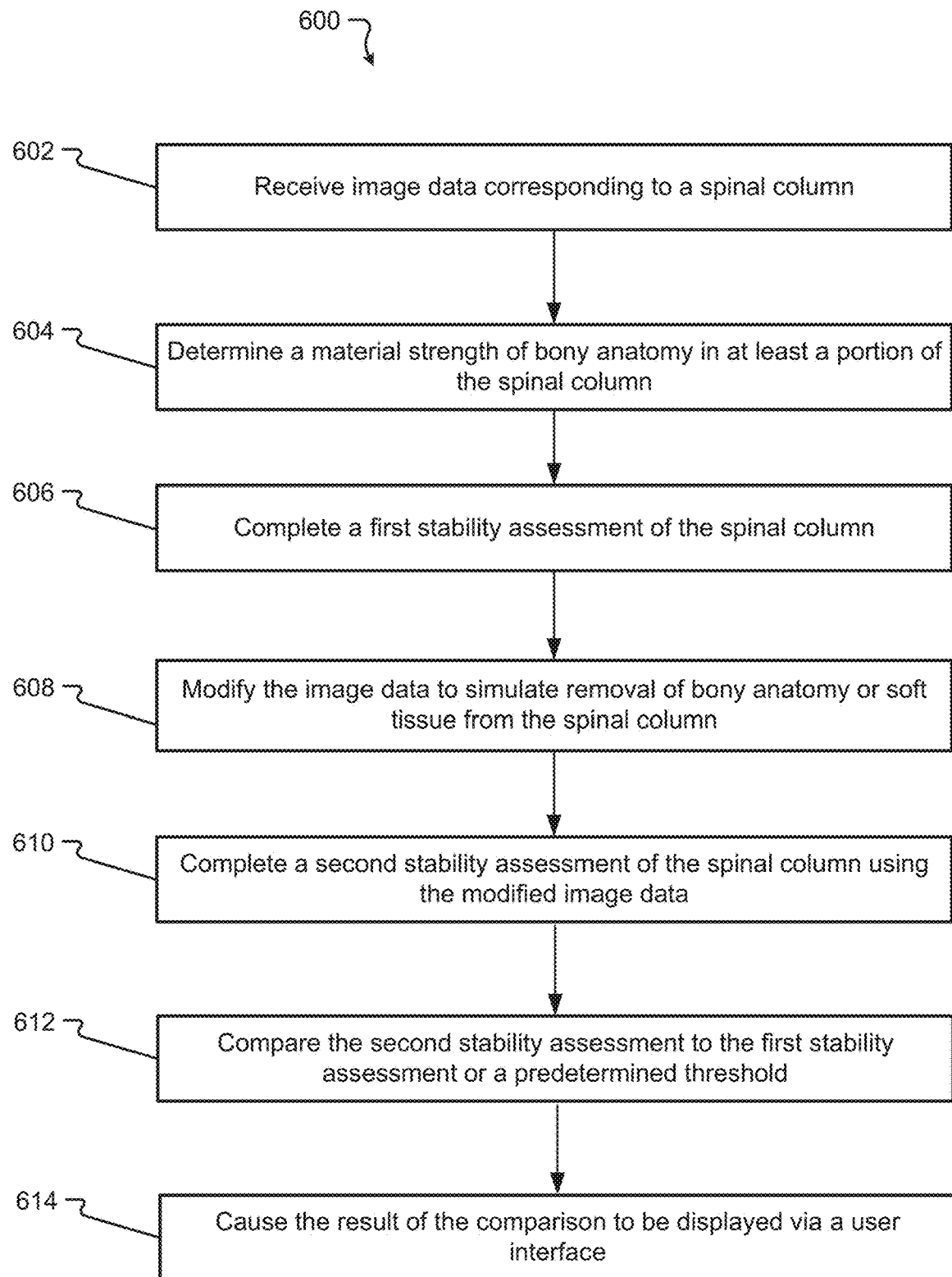
FIG. 6 is another flowchart of a method according to at least one embodiment of the present disclosure.

Turning now to FIG. 6, a method 600 of assessing spinal column integrity comprises receiving image data corresponding to a spinal column (step 602). The receiving image data corresponding to a spinal column may be accomplished in the same manner as or in a similar manner to step 202 of the method 600. For example, the image data may comprise or correspond to, for example, a three-dimensional image of a spinal column of a patient, and may comprise data corresponding to a plurality of individual cuts, slices, or sections of the spinal column of the patient that together make up the three-dimensional image of the spinal column. Additionally or alternatively, the image data may comprise or correspond to one or more two-dimensional images of the spinal column of the patient. For example, the preoperative image data may correspond to images such as the image 300 of FIG. 3A, and/or the image 302 of FIG. 3B. Where the image data comprises or corresponds to a plurality of two-dimensional images of the spinal column of the patient, the plurality of two-dimensional images may be sufficient to construct or reconstruct a three-dimensional image or model of the spinal column. The preoperative image data may correspond to a preoperative image taken of the spinal column of the patient using an imaging device 112, such as an MRI scanner, a CT scanner, or another imaging device. The preoperative image data may contain data for an entire spinal column of the patient or for a portion of the spinal column of the patient. The preoperative image data may be received from an imaging device 112, a database 114, the cloud 114, or any other source, and may be received via the communication interface 108.

The method 600 also comprises determining a material strength or stiffness of bony anatomy in at least a portion of the spinal column (step 604). The material strength or stiffness may be determined by processing the image data (e.g., in one or more of the ways described above with respect to the step 202 of the method 200), and/or by analyzing metadata included with the image data. Where the image data corresponds to a plurality of slices (which plurality of slices yields, for example and when taken together, a 3D image), the determining a material strength or stiffness of bony anatomy may comprise determining a material strength or stiffness of the bony anatomy in each of the plurality of slices. The material strength or stiffness of a given portion of bony anatomy in the image data may be determined by measuring the Hounsfield units of that portion of bony anatomy in the image data, and/or by completing a bone mineral density test or similar analysis. In some embodiments, the image data may include data corresponding to an imaged phantom having a known material strength or stiffness (or having different portions, each with a known material strength or stiffness), and the material strength or stiffness of a given portion of bony anatomy may be determined by comparing a pixel intensity or other characteristic of the given portion of bony anatomy to the pixel intensity or other corresponding characteristic of the image data corresponding to the phantom (or a portion thereof).

The method 600 further comprises completing a first stability assessment of the spinal column (step 606). The stability assessment may be completed in the same manner as or in a similar manner to the stability assessment completed in step 212 of the method 200. For example, assessing the stability of the spinal column may comprise running a virtual 6-degrees of motion analysis based on the image data to assess a preoperative stability of the spinal column. The analysis may evaluate the stresses imposed on one or more vertebrae of the spinal column represented in the image data while the spinal column is in a neutral position and/or while the spinal column is in one or more positions of flexion. The result of a virtual 6-degrees of motion analysis may be a calculated level of stability of the spinal column; an indication of the maximum stress imposed on one or more vertebrae of the spinal column; an indication that a level of stress for one or more vertebrae of the spinal column exceeds a predetermined threshold (even prior to any decompression procedure or other operation); or any other indication relating to the preoperative stability or instability of the spinal column represented in the image data.

In some embodiments, the step 606 may comprise generating a virtual three-dimensional model of the spinal column based on the image data. The various anatomical elements of the spinal column included in the virtual three-dimensional model (or portions thereof) may be assigned a material strength or stiffness determined for that anatomical element (or portion thereof) in the step 604. The virtual 6-degrees of motion analysis may then be conducted on and/or using the virtual 3D model, with the same result or results described above.

The method 600 also comprises modifying the image data to simulate removal of bony anatomy and/or soft tissue from the spinal column (step 608). The modifying may comprise identifying bony anatomy and/or soft tissue to be removed from the spinal column to correct an identified stenosis or other condition of the spinal column, which may be done in the same manner as or in a similar manner to that described above in connection with the step 208 of the method 200. For example, in some embodiments, an algorithm may be used to identify bony anatomy and/or soft tissue that needs to be removed to correct a stenotic condition. The bony anatomy may be, for example, a portion of one or more vertebrae, and the soft tissue may be, for example, all or part of a disc, a ligament, or other soft tissue.

In some embodiments, the identifying of bony anatomy and/or soft tissue to be removed may comprise receiving user input (e.g., from a surgeon or other user) via a user interface that identifies the bony anatomy and/or soft tissue to be removed. For example, the user input may comprise a user selection of one of a laminotomy, laminectomy, foraminotomy, discectomy, or other procedure. Based on the user selection, a recommended portion of bony anatomy and/or soft tissue may be automatically identified for removal, or the surgeon or other user may identify the portion of bony anatomy and/or soft tissue to be removed. For example, if the user input is a laminectomy, a lamina of a vertebra proximate the identified stenosis may be automatically identified for removal, or the user may select a lamina of a vertebra for removal.

Often, the bony anatomy or soft tissue that needs to be removed in a decompression procedure is not readily accessible to a surgeon. As a result, the surgeon must remove additional bony anatomy and/or soft tissue from the spinal column simply to access the bony anatomy and/or soft tissue causing the stenosis. In some embodiments, then, identification of the bony anatomy and/or soft tissue to be removed includes not only identifying the bony anatomy and/or soft tissue that needs to be removed to correct the stenosis, but also the bony anatomy and/or soft tissue that needs to be removed to access the stenosis-causing bony anatomy and/or soft tissue. The bony anatomy and/or soft tissue that must be removed to access the stenosis-causing bony anatomy and/or soft tissue may be identified automatically (e.g., by applying an algorithm selected based on the procedure to be completed and/or predefined by a machine learning engine or otherwise) or via additional user input.

The identifying step 208 may further comprise marking the identified bony anatomy and/or soft tissue in the image data (or, where a virtual 3D model of the spinal column is being used, marking the identified bony anatomy and/or soft issue in the virtual 3D model).

Once the bony anatomy and/or soft tissue to be removed has been identified, the modifying may occur in the same manner as or in a similar manner to the step 210 of the method 200. For example, modifying the image data to simulate removal of the bony anatomy and/or soft tissue may comprise substituting, in the image data, a virtual material having little or no material strength or stiffness for the identified bony anatomy and/or soft tissue. Alternatively, modifying the image data to simulate removal of the bony anatomy and/or soft tissue may comprise simply deleting the portion of the image data representing the bony anatomy and/or the soft tissue to be removed. As another alternative, the virtual removal of the bony anatomy and/or soft tissue may comprise assigning a Hounsfield units measurement of zero to the portion of the image data representing the bony anatomy and/or the soft tissue to be removed.

In embodiments where a virtual 3D model is used for the first stability assessment in step 606, the step 608 may comprise modifying the virtual 3D model (rather than the image data) to simulate removal of bony anatomy and/or soft tissue from the spinal column. The simulated removal of bony anatomy and/or soft tissue from the spinal column in the virtual 3D model may comprise simply deleting from the model that portion of each vertebra, disc, ligament, or other bony anatomy and/or soft tissue that corresponds to the bony anatomy and/or soft tissue to be removed.

The method 600 further comprises completing a second stability assessment of the spinal column using the modified image data (step 610). The second stability assessment may be completed in the same manner as or in a similar manner to the first stability assessment in step 606, except that the second stability assessment is based on the modified image data (or, in embodiments, where a virtual 3D model is being used, based on the modified virtual 3D model). The types of results of the second stability assessment may also be the same as or similar to the types of results described above in connection with the first stability assessment.

The method 600 also comprises comparing the second stability assessment to the first stability assessment or a predetermined threshold (step 612). The comparison may comprise comparing a calculated preoperative level of stability of the spinal column to a calculated or predicted postoperative level of stability of the spinal column; comparing an indication of the preoperative maximum stress imposed on one or more vertebrae of the spinal column to an indication of the postoperative maximum stress predicted to be imposed on one or more vertebrae of the spinal column; or a comparison of any other indication relating to the preoperative and postoperative stability of the spinal column represented in the image data and/or in the virtual 3D model. In embodiments where the results of the first stability assessment and the second stability assessment each comprise an indication that is based on one or more predetermined thresholds, the comparison may comprise evaluating whether the indication has remained the same (e.g., that no change in stability of the spinal column is expected), has changed for the better, or has changed for the worse. In other embodiments where the results of the first stability assessment and the second stability assessment each comprise an indication that is based on one or more predetermined thresholds, the step 612 may not be needed.

The method 600 further comprises causing the result of the comparison to be displayed via a user interface (step 614). The result of the comparison may be displayed via a user interface such as the user interface 110. The result may be displayed as a number, a range, a color-coded indication (e.g., green for a low risk of postoperative iatrogenic instability, yellow for a medium risk of postoperative iatrogenic instability, and red for a high risk of postoperative iatrogenic instability), as text (e.g., indicating that the postoperative risk of iatrogenic instability is high, medium, or low), in graphical form (e.g., as a meter showing a plurality of possible results, with an arrow or other marker indicating the actual result), in any other manner, and/or in any combination of any of the foregoing manners. In embodiments where the second stability assessment comprised comparing a calculated or measured value to a predetermined threshold (e.g., to determine whether a postoperative risk of iatrogenic instability is high, medium, or low), information corresponding to that comparison (such as, for example, the result of the comparison and/or the information used to make the comparison) maybe displayed via the user interface.

Figure 7:
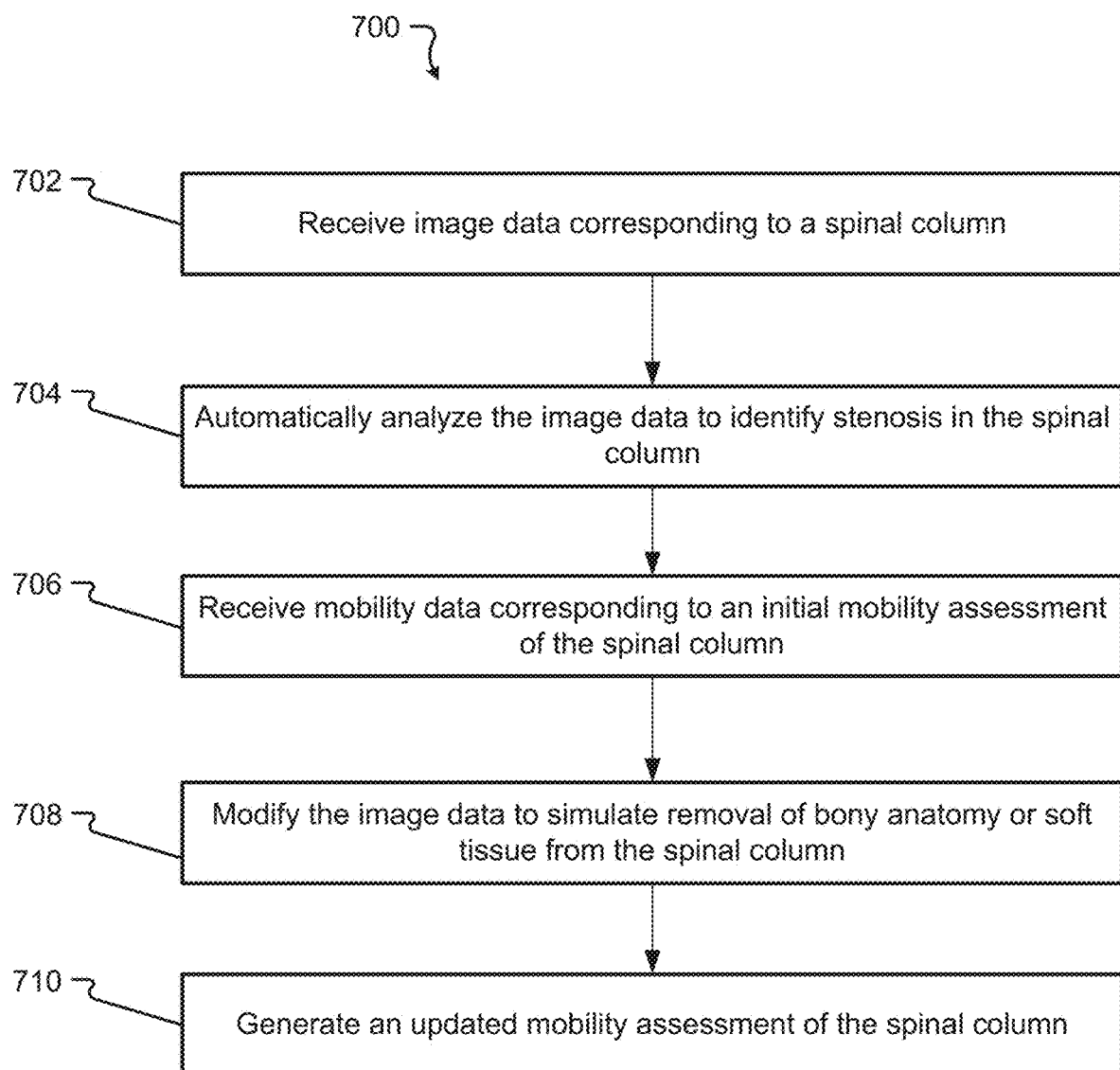
FIG. 7 is another flowchart of a method according to at least one embodiment of the present disclosure.

Turning now to FIG. 7, a method 700 of assessing spinal column integrity comprises receiving image data corresponding to a spinal column (step 702). The receiving image data corresponding to a spinal column may be accomplished in the same manner as or in a similar manner to step 602 of the method 600 and/or step 202 of the method 200. In some embodiments, the image data may comprise a virtual three-dimensional model of the spinal column that was generated based on actual images of the spinal column of the patient. In other embodiments, the step 702 may comprise generating a virtual three-dimensional model of the spinal column based on the image data.

The method 700 also comprises automatically analyzing the image data to identify stenosis in the spinal column (step 704) or, in embodiments where a virtual 3D model of the spinal column is generated based on the image data, automatically analyzing the virtual 3D model to identify stenosis in the spinal column. The stenosis may be identified in the central canal and/or in a lateral recess of the spinal column represented by the image data. The automatically analyzing the image data to identify stenosis in the spinal column may be accomplished in the same manner as or in a similar manner to in step 204 of the method 200. For example, in some embodiments, the stenosis may be identified by comparing image data corresponding to a first portion of a spinal column to image data corresponding to a second portion of the spinal column that is different than the first portion of the spinal column. As a more specific example, the stenosis may be identified by comparing a diameter of the spinal cord at a first level of the spinal column with a diameter of the spinal cord at one or more other levels of the spinal column, which one or more other levels may be adjacent the first level. A sudden or rapid change in the diameter of the spinal column between or among adjacent or proximate levels may indicate stenosis.

In other embodiments, the stenosis may be identified by applying a predefined algorithm to the image data. The algorithm may be or have been generated, for example, by a machine learning engine based on training data.

The method 700 further comprises receiving mobility data corresponding to an initial mobility assessment of the spinal column (step 706). The mobility data may be received together with or separately from the image data received in the step 702. The mobility data may be based on a mobility assessment completed independently of the image data, or a mobility assessment based on the image data. The mobility data may correspond to a 6-degrees of motion assessment, and/or to an assessment of a maximum flexion/extension of the spinal column in a lateral plane and/or an anterior-posterior plane and/or around a vertical axis.

The method 700 also comprises modifying the image data to simulate removal of bony anatomy and/or soft tissue from the spinal column (step 708). The modifying the image data may be accomplished in the same manner as or in a similar manner to the step 608 of the method 600 and/or step 210 of the method 200. The simulated removal of bony anatomy and/or of soft tissue from the spinal column may be based on the stenosis identified in step 704 and may involve removing the bony anatomy and/or soft tissue that is causing the identified stenosis. The simulated removal of bony anatomy and/or soft tissue may further involve removing bony anatomy and/or soft tissue to enable access to the bony anatomy and/or soft tissue that is causing the identified stenosis.

In some embodiments, the simulating removal of bony anatomy and/or soft tissue from the spinal column may be based on a user input (e.g., from a surgeon or other user) received via a user interface (such as the user interface 110) that identifies the bony anatomy and/or soft tissue to be removed. For example, the user input may comprise a user selection of one of a laminotomy, laminectomy, foraminotomy, discectomy, or other procedure. Based on the user selection, a recommended portion of bony anatomy and/or soft tissue may be automatically identified for removal, or the surgeon or other user may identify the portion of bony anatomy and/or soft tissue to be removed. For example, if the user input is a laminectomy, a lamina of a vertebra proximate the identified stenosis may be automatically identified for removal, or the user may select a lamina of a vertebra for removal.

In some embodiments (e.g., where the image data does not comprise a virtual 3D model of the spinal column, and the step 702 does not comprise generating such a virtual 3D model), the step 706 may comprise generating a virtual three-dimensional model of the spinal column based on the image data. The various anatomical elements of the spinal column included in the virtual three-dimensional model (or portions thereof) may be modified to simulate removal of bony anatomy and/or soft tissue from the spinal column.

The method 700 further comprises generating an updated mobility assessment of the spinal column (step 710). The updated mobility assessment may be completed based on the modified image data (or modified virtual 3D model) resulting from the step 708. The updated mobility assessment may correspond to a 6-degrees of motion assessment, and/or to an assessment of a maximum flexion/extension of the spinal column in a lateral plane and/or an anterior-posterior plane and/or around a vertical axis.

Depending on the results of the updated mobility assessment of the spinal column, which may be displayed or otherwise reported to a surgeon or other user, a determination may be made as to whether a predicted risk of postoperative iatrogenic instability of the spinal column is high enough to justify planning and/or completing a spinal fusion procedure or other procedure to improve the stability of the spinal column. The method 700 thus beneficially facilitates an objective evaluation of whether a decompression or other spinal procedure will likely result in iatrogenic instability, and whether a spinal fusion or other procedure to improve spinal stability is or is likely to be needed following the initial procedure.

Although the foregoing disclosure has focused primarily on correcting compression of a spinal cord, the systems and methods disclosed herein may be used to correct compression of a traversing or exiting nerve as well. Moreover, the systems and methods disclosed herein may be used to assess a risk of iatrogenic instability in connection with any spinal procedure, not just decompression procedures intended to correct a stenotic condition.

Figure 2:
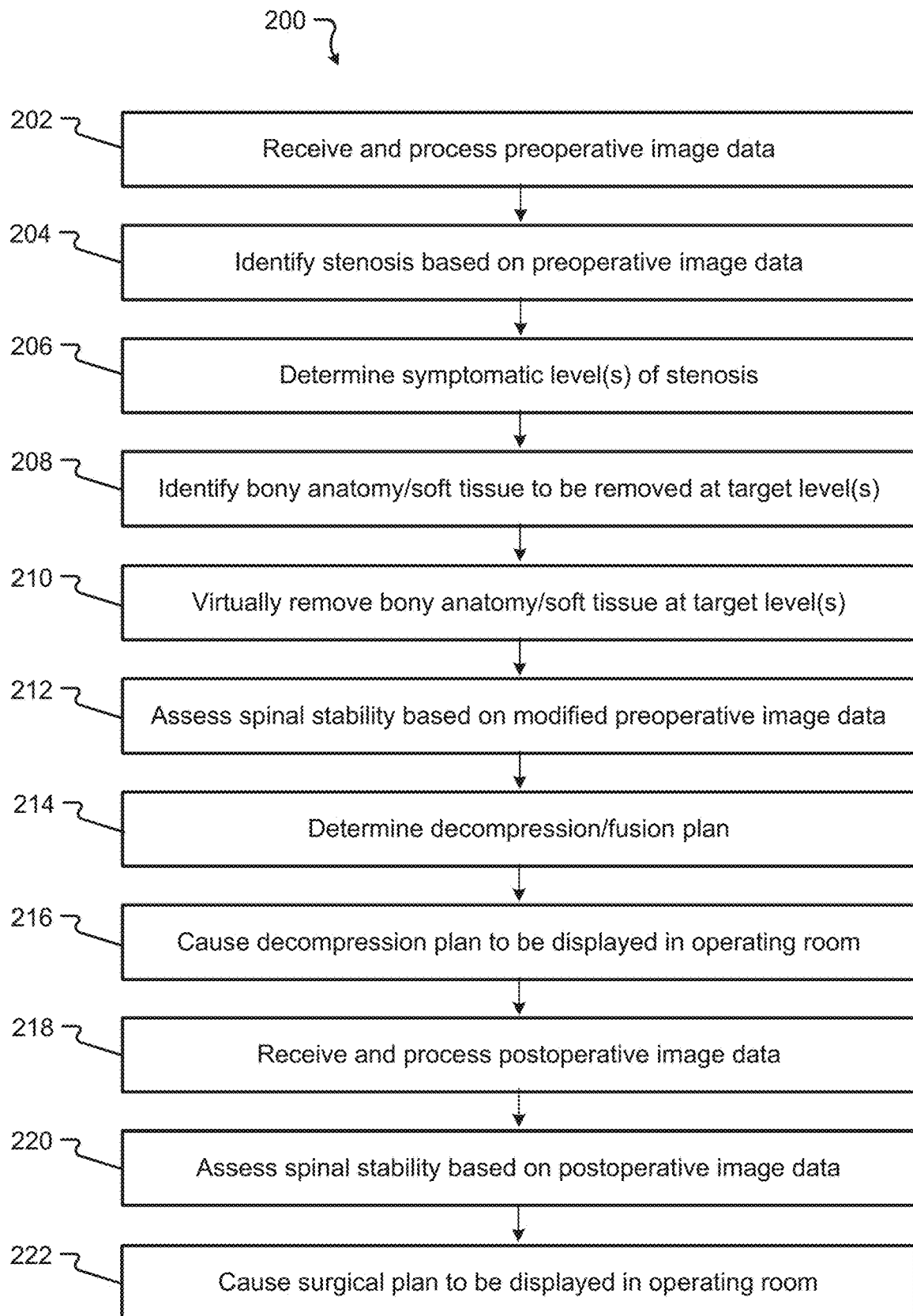
FIG. 2 is a flowchart of a method according to at least one embodiment of the present disclosure.
Figure 3B:
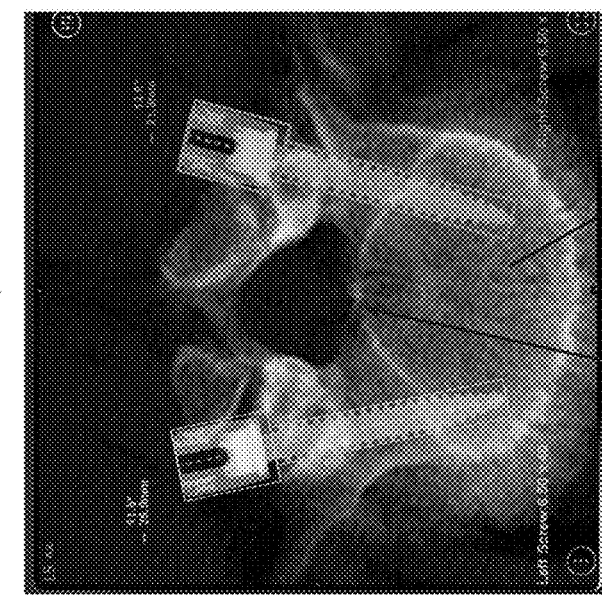
FIG. 3B is a superior image of a vertebra within the spine region of FIG. 3A, according to at least one embodiment of the present disclosure.
Figure 3A:
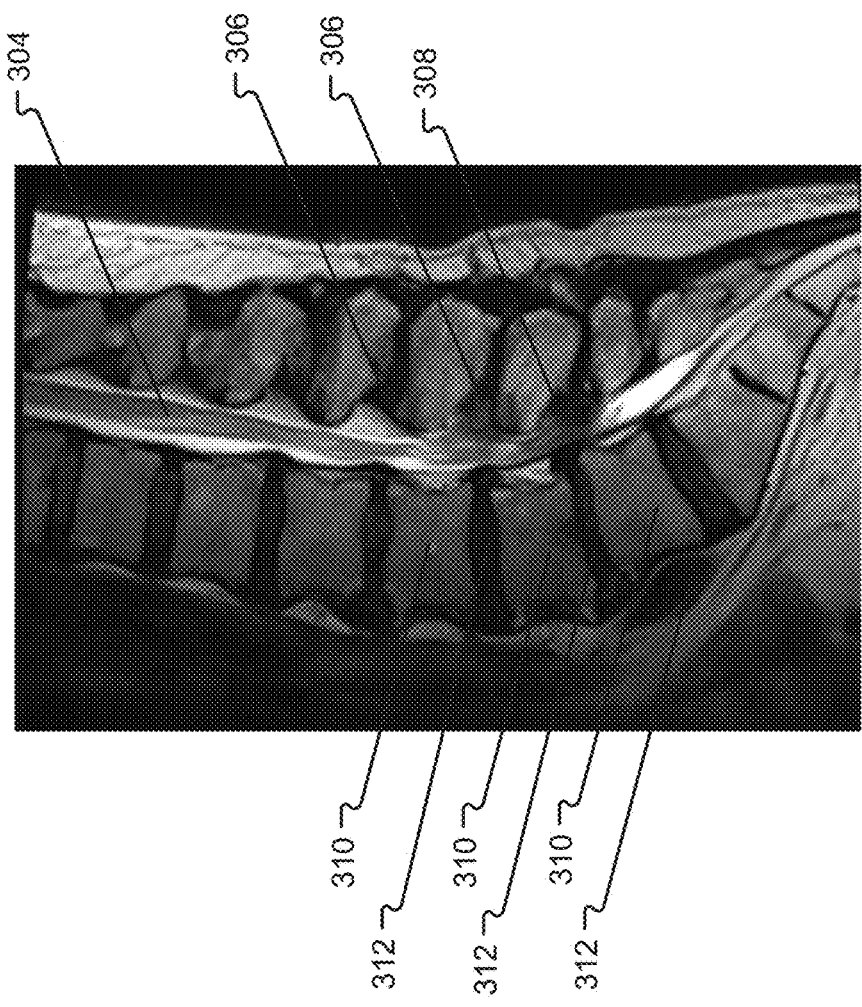
FIG. 3A is a lateral image of a spine region according to at least one embodiment of the present disclosure.

As may be appreciated based on the foregoing disclosure, the present disclosure encompasses methods with fewer than all of the steps identified in FIGS. 2, 6, and 7 (and the corresponding description), as well as methods that include steps from more than one of FIGS. 2, 6, and 7 (and the corresponding description).

In some embodiments, one or more steps of any of the methods 200, 600, and/or 700 may be repeated one or more times, e.g., to allow a surgeon or other user to test the effect on predicted spinal integrity of a plurality of different procedures or implementations of a given procedure.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of assessing spinal column stability, comprising:
   receiving image data corresponding to a spinal column of a patient;
   determining, based on the image data, a material strength of bony anatomy in at least a portion of the spinal column;
   completing a first stability assessment of the spinal column, based at least in part on the determined material strength, the first stability assessment being indicative of a preoperative stability of the spinal column;
   modifying the image data to simulate removal of bony anatomy or soft tissue from the spinal column to yield modified image data; and
   completing a second stability assessment of the spinal column, based at least in part on the determined material strength and the modified image data, the second stability assessment being indicative of a predicted postoperative stability of the spinal column.

2. The method of claim 1, further comprising:
   comparing the second stability assessment to the first stability assessment; and
   causing information corresponding to the comparison to be displayed via a user interface.

3. The method of claim 1, further comprising:
   comparing the second stability assessment to a predetermined threshold; and
   causing information corresponding to the comparison to be displayed via a user interface.

4. The method of claim 3, wherein the information corresponding to the comparison is an indication that a risk of instability is high, medium, or low.

5. The method of claim 1, wherein the image data corresponds to a 3D image of the spinal column, the 3D image comprising a plurality of slices, and further wherein the determining comprises determining a material strength of bony anatomy in each of the plurality of slices.

6. The method of claim 1, wherein the simulated removal of bony anatomy or soft tissue from the spinal column corresponds to a received user selection of one of a laminectomy, a laminotomy, or a foraminotomy.

7. The method of claim 1, wherein the simulated removal of bony anatomy or soft tissue from the spinal column corresponds both to removal of first bony anatomy or soft tissue from the spinal column to correct stenosis, and to removal of second bony anatomy or soft tissue from the spinal column to enable access to the first bony anatomy or soft tissue.

8. The method of claim 1, wherein the image data corresponds to a plurality of 2D images of the spinal column.

9. The method of claim 1, wherein the image data corresponds to a CT scan, and wherein determining the material strength of bony anatomy in at least the portion of the spinal column is based on a measurement in Hounsfield units of the bony anatomy.

10. A method of assessing spinal column stability, comprising:
   receiving image data corresponding to a spinal column of a patient;
   receiving mobility data corresponding to an initial mobility assessment of the spinal column, the initial mobility assessment being indicative of a preoperative stability of the spinal column;
   modifying, based on a user input, the image data to simulate removal of bony anatomy or soft tissue from the spinal column to yield modified image data; and
   generating an updated mobility assessment of the spinal column, based on the modified image data, the updated mobility assessment being indicative of a predicted postoperative stability of the spinal column.

11. The method of claim 10, further comprising:
   automatically analyzing the image data to identify stenosis in the spinal column.

12. The method of claim 11, wherein the automatic analysis is based on a comparison of image data corresponding to a first portion of the spinal column to image data corresponding to a second portion of the spinal column, the second portion being different than the first portion.

13. The method of claim 11, wherein the automatic analysis utilizes a predefined algorithm.

14. The method of claim 11, wherein the simulated removal of bony anatomy or soft tissue from the spinal column is based on the identified stenosis.

15. The method of claim 10, wherein the user input corresponds to a user selection of one of a laminectomy, a laminotomy, or a foraminotomy.

16. The method of claim 10, wherein the simulated removal of bony anatomy or soft tissue from the spinal column corresponds both to removal of first bony anatomy or soft tissue from the spinal column to correct stenosis, and to removal of second bony anatomy or soft tissue from the spinal column to enable access to the first bony anatomy or soft tissue.

17. A system for assessing spinal column stability, comprising:
   a communication interface;
   a processor; and
   a memory, the memory storing instructions for execution by the processor that, when executed, cause the processor to:
      receive preoperative image data corresponding to a spinal column of a patient in a first state;
      identify spinal stenosis in a region of the spinal column based on the preoperative image data;
      generate a first stability assessment for the region of the spinal column based on the preoperative image data, the first stability assessment being indicative of a preoperative stability of the spinal column;
      determine a portion of bony anatomy or soft tissue to remove to correct the spinal stenosis;
      simulate removal of the portion of bony anatomy or soft tissue to yield modified preoperative image data; and
      generate a second stability assessment of the spinal column based on the modified preoperative image data, the second stability assessment being indicative of a predicted postoperative stability of the spinal column.

18. The system of claim 17, wherein the memory stores additional instructions that, when executed, further cause the processor to:
   receive postoperative image data corresponding to the spinal column of the patient, the postoperative image data reflecting removal of some bony anatomy or soft tissue relative to the preoperative image data; and
   generate a third stability assessment of the spinal column based on the postoperative image data.

19. The system of claim 17, wherein the memory stores additional instructions that, when executed, further cause the processor to:
   generate a decompression surgical plan to correct the spinal stenosis; and
   cause the decompression surgical plan to be displayed on a user interface.

20. The system of claim 17, wherein the memory stores additional instructions that, when executed, further cause the processor to:
   determine a spinal column level of the spinal stenosis.

* * * * *